United States Patent
Bressler et al.

(10) Patent No.: US 6,918,891 B2
(45) Date of Patent: Jul. 19, 2005

(54) SAFETY DEVICE

(76) Inventors: Peter Bressler, 816 S. 10th St., Philadelphia, PA (US) 19147; John D. Coleman, 4650 Sheldon Ave., Philadelphia, PA (US) 19127; Mathieu Turpault, 409 Berwyn Baptist Rd., Berwyn, PA (US) 19312

( * ) Notice: Subject to any disclaimer, the term of this patent is extended or adjusted under 35 U.S.C. 154(b) by 138 days.

(21) Appl. No.: 10/392,734

(22) Filed: Mar. 19, 2003

(65) Prior Publication Data

US 2003/0181875 A1 Sep. 25, 2003

Related U.S. Application Data

(60) Provisional application No. 60/366,702, filed on Mar. 21, 2002.

(51) Int. Cl.[7] .................................................. A61M 5/32
(52) U.S. Cl. ...................................... 604/198; 604/177
(58) Field of Search .............................. 604/177, 198, 604/263, 174, 192, 165.03, 179

(56) References Cited

U.S. PATENT DOCUMENTS

| 4,929,241 A | 5/1990 | Kulli |
| 5,348,544 A | * 9/1994 | Sweeney et al. ............. 604/192 |
| 5,423,766 A | 6/1995 | Di Cesare |
| 5,549,571 A | 8/1996 | Sak |
| 5,584,818 A | 12/1996 | Morrison |
| 5,814,018 A | 9/1998 | Elson et al. |
| 5,925,020 A | 7/1999 | Nestell |
| 5,957,892 A | 9/1999 | Thorne |
| 5,980,488 A | 11/1999 | Thorne |
| 6,234,999 B1 | 5/2001 | Wemmert et al. |
| 6,254,575 B1 | 7/2001 | Thorne, Jr. et al. |
| 2001/0039401 A1 | 11/2001 | Ferguson et al. |

FOREIGN PATENT DOCUMENTS

WO   WO 00/16832   of 2000

* cited by examiner

*Primary Examiner*—Kevin C. Sirmons

(57) ABSTRACT

A safety needle assembly has a hub and a needle cannula that projects distally from the hub. A shield is mounted on the needle cannula and can move from a proximal position adjacent the hub and a distal position for shielding the tip of the needle cannula. A fin projects from the hub to facilitate digital manipulation of the needle assembly. A proximal arm is hinged to the hub and a distal arm is hinged to both the proximal arm and the shield. The proximal arm is releasably engaged with the fin when the shield is in the proximal position. However, digital forces on the arms enables the shield to be propelled to the distal position.

21 Claims, 3 Drawing Sheets

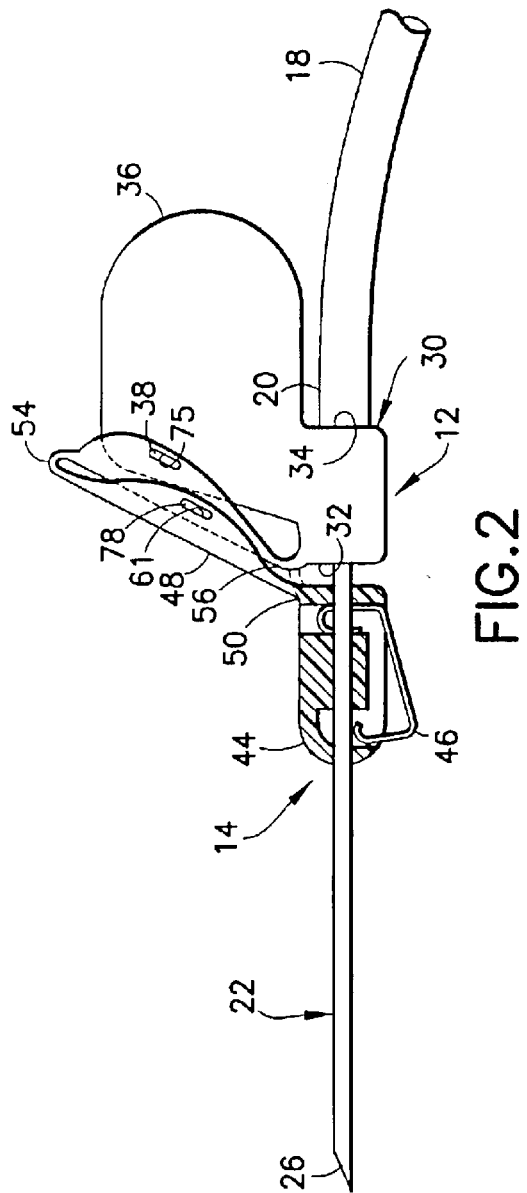
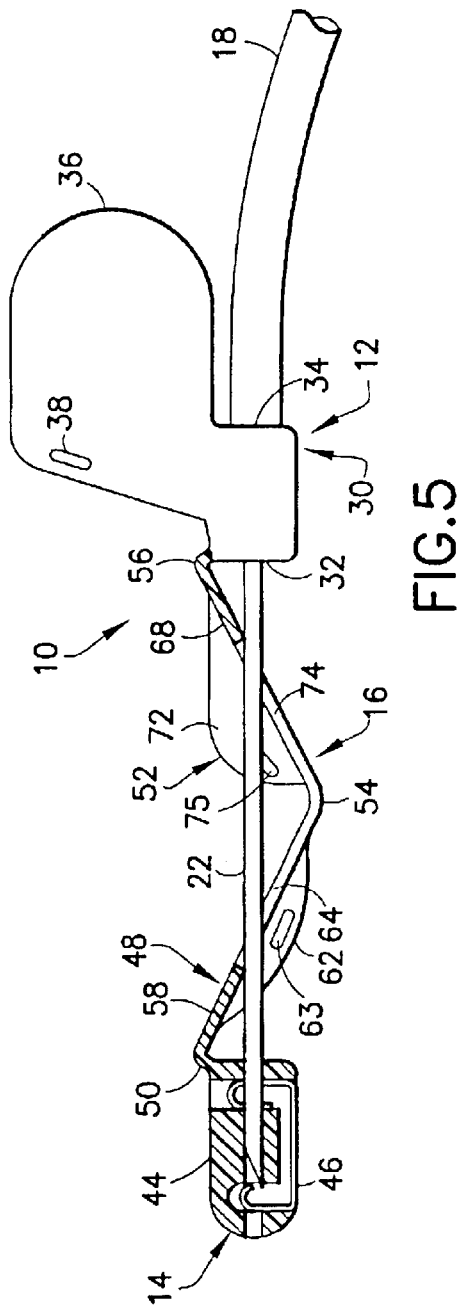

SAFETY DEVICE

RELATED APPLICATIONS

This application claims priority on U.S. Provisional Patent Appl. No. 60/366,702 filed Mar. 21, 2002.

FIELD OF THE INVENTION

The subject invention relates to safety shields for hypodermic needles, blood collection needles, catheter needles and other medical implements to prevent accidental needle sticks.

BACKGROUND OF THE INVENTION

Safety shields are employed widely in the health care industry to eliminate or reduce the risk of accidental needle sticks. Safety shields have taken many forms, including shields that telescope along the needle cannula from a proximal position to a distal position. The distal tip of the needle cannula is exposed for use when the shield is in the proximal position. However the pointed distal tip of the needle cannula is covered when the shield is in the distal position.

Some shields are large and telescope over a syringe, needle holder or other medical implement. Some such large shields also include coil springs to propel the shield distally. The spring typically is locked in a collapsed condition around proximal portions of the medical implement when the shield is retained in the proximal position. An actuator is triggered after use of the medical implement to release the spring and drive the shield distally into a shielding disposition around the needle cannula.

Other shields are much smaller and are configured to telescope only along the needle cannula. The shield in these prior art devices may be connected to the syringe or the needle hub by a tether or a linked array of hinged arms to limit the range of movement of the shield relative to the needle cannula. Thus, the shield can be moved distally into surrounding relationship with the tip of the needle cannula. However, the tether or hinged arms prevent the shield from sliding completely off the needle cannula. Some shield assemblies of this general type include a spring mechanism for assisting a portion of the distal movement of the shield along the needle cannula. A shielding assembly of this general type is shown in U.S. Pat. No. 5,348,544 which is assigned to the assignee of the subject invention. The shielding assembly shown in U.S. Pat. No. 5,348,544 requires the user to initiate shielding by exerting digital pressure on one of the hingedly connected arms. This initial digital pressure will be resisted by the spring. However, after a certain range of movement, the hingedly connected arms will be positioned such that the spring assists the distal movement of the shield. The needle shielding device shown in U.S. Pat. No. 5,348,544 is very effective.

Some medical procedures employ a wing set for collecting fluid from a patient or delivering fluid to a patient. A wing set typically includes a length of flexible plastic tubing. One end of the tubing communicates either with a supply of fluid that will be delivered intravenously to the patient or with a container that will receive blood or other fluids drawn from the patient. The wing set further includes a needle assembly. The needle assembly includes a needle hub that has opposite proximal and distal ends. The proximal end of the hub is securely mounted to the end of the flexible plastic tubing remote from the container. The needle cannula is mounted to and projects from the distal end of the needle hub. The needle assembly of the typical wing set also includes a shield that is telescoped over the needle hub and that can be moved from a proximal position where the needle cannula is exposed to a distal position where the needle cannula is shielded. The needle assembly further includes at least one wing that projects from the needle hub or from the shield. The wing facilitates digital manipulation of the needle assembly. The wing also can be used to tape the needle assembly to the skin of the patient. Many needle assemblies include a pair of flexible wings that can be folded into face-to-face relationship with one another to facilitate digital manipulation. However, the wings can be folded into a coplanar disposition for taping the needle assembly to the skin of the patient.

SUMMARY OF THE INVENTION

The subject invention is directed to a wing set assembly with a needle hub, a needle cannula projecting from the hub and a shield configured for shielding at least portions of the needle cannula.

The hub may be molded from plastic and includes opposite proximal and distal ends and a passage extending between the ends. The proximal end of the hub may be mounted to a length of flexible plastic tubing. Gripping means may extend transversely from the hub to facilitate digital manipulation of the wing set. The gripping means comprises a dorsal fin and/or wings. The wings may be substantially rigid. Alternatively, the wings may be rotatable or flexible relative to the hub and may have an unbiased condition where the wings are substantially coplanar. However, the wings may be rotated or deflected relative to the hub into substantially face-to-face relationships so that the wings can be squeezed between a thumb and forefinger to facilitate digital manipulation of the wing set.

The needle cannula comprises a proximal end and a distal end. The proximal end of the needle cannula may be mounted securely in the distal end of the hub so that a lumen through the needle cannula communicates both with the passage through the hub and with the plastic tubing. The distal end of the needle cannula is sufficiently pointed for penetrating skin and adjacent tissue of a patient.

The shield of the wing set may be slidably movable along the needle cannula from a proximal position substantially adjacent the hub to a distal position for shielding the distal tip of the needle cannula. The wing set further comprises connection means for limiting movement of the shield along the needle cannula. The connection means may comprise a flexible tether or a plurality of hingedly articulating arms that can move from a collapsed condition to an extended condition. The connection means is in the collapsed condition when the shield is in its proximal position relative to the needle cannula. However, the connection means is in a fully extended condition when the shield has advanced into shielding disposition around the tip of the needle cannula.

The connection means may comprise a distal end that is articulated to the shield and a proximal end that is articulated to or near the needle hub. More particularly, the proximal end of the connection means may be articulated directly to the needle hub. Alternatively, the proximal end of the connection means may be articulated to a base which, in turn, is connected securely to the needle hub.

The wing set may further comprise a biasing means for urging the shield from the proximal position to the distal position. The biasing means may comprise a torsion spring mounted between a plurality of hingedly connected arms of the connection means. Alternatively, the biasing means may comprise a coil spring that surrounds the needle cannula at locations between the shield and the needle hub. The biasing means may be disposed and configured for having stored energy when the safety shield is in its proximal position. Additionally, the biasing means may be configured relative to the shield and the connection means such that the stored energy will urge the shield distally at all points along the range of movement of the shield. Thus, the biasing means may be configured and disposed for urging the shield distally even when the shield is in its extreme proximal position. Accordingly, the biasing means may avoid the need to initially exert digital pressure on the shield or on a hinged arm to start the shield moving toward the distal shielding position. Alternatively, the biasing means may comprise an over-center hinge that initially biases the shield toward the proximal position. Digital force can be used to rotate the over center hinge into a position where the inherent biasing force urges the shield toward and into the distal position.

The wing set may further comprise latching means for releasably retaining the shield in the proximal position. The latching means may comprise a first part on the connection means and a second part on the gripping means. For example, the connection means may be configured to releasably engage a dorsal fin when the shield is in its proximal position. However, forces exerted on the connection means or on the latching means may be sufficient to overcome the retention forces between the connection means and the dorsal fin. Thus, the shield can be moved to the distal position.

The wing set of the subject invention may further comprise a safety cap that is removably engaged over the needle cannula prior to use. The safety cap may be formed from a rigid plastic material and may be dimensioned to cover the entirety of the needle cannula from the distal end to the proximal end. Proximal portions of the safety cap may be dimensioned for removable frictional engagement over the shield. Alternatively, the safety cap may pass through the shield and may be removably engaged with the hub. The safety cap prevents accidental sticks with the needle cannula prior to use.

The shield of the subject wing set initially is latched or otherwise retained in its proximal position on the needle cannula with the connecting means in a collapsed condition. The safety cap then is mounted over the needle cannula sufficiently for removable frictional engagement of the safety cap with either the needle hub or the shield. This initial positioning of the shield and the safety cap is carried out at the place of manufacture and does not require any action by the health care worker. Similarly, a length of flexible plastic tubing may be connected to the needle hub at the place of manufacture. The wing set then is packaged and shipped.

A health care worker may use the wing set substantially in a conventional manner. In particular, the end of the plastic tubing remote from the needle assembly may be connected to a container. The health care worker then secures the gripping means between a thumb and forefinger and removes the safety cap from the needle cannula. The pointed distal end of the needle cannula then is guided into a selected injection site. Wings that may project from the needle hub can be taped to the skin of the patient to hold the wing set in place.

The needle cannula is removed from the patient after an appropriate volume of liquid has been withdrawn or after an appropriate dosage of a liquid has been administered. The health care worker then activates the latching means so that the shield is no longer retained in the proximal position and can be moved distally into shielding position around the tip of the needle cannula. Actuation of the latching means may require digital manipulation of a latch. Alternatively, actuation of the latching means may require the mere exertion of distally directed forces on either the connection means or the shield sufficient to overcome the latching forces. The health care worker may continue to exert distally directed forces on the shield or the connection means until the shield reaches the distal position. Alternatively, spring means may propel the shield to the distal position after the actuation of the latch means. The safely shielded wing set then can be separated from the container and discarded into an appropriate sharps receptacle.

BRIEF DESCRIPTION OF THE DRAWINGS

FIG. 2 is a side elevational view, partly in section, of the wing set in the condition shown in FIG. 1.

FIG. 5 is a side elevational view, partly in section, and showing the shield in the condition illustrated in FIG. 4.

DETAILED DESCRIPTION OF THE INVENTION

Figure 1:
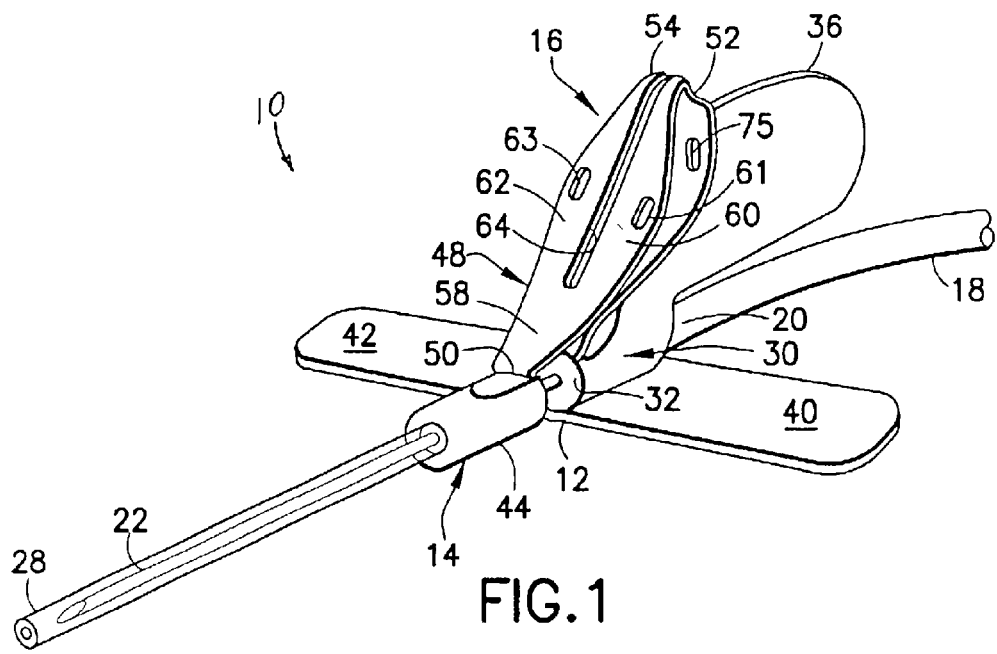
FIG. 1 is a perspective view of a wing set in accordance with the subject invention with the shield in a proximal position.
Figure 3:
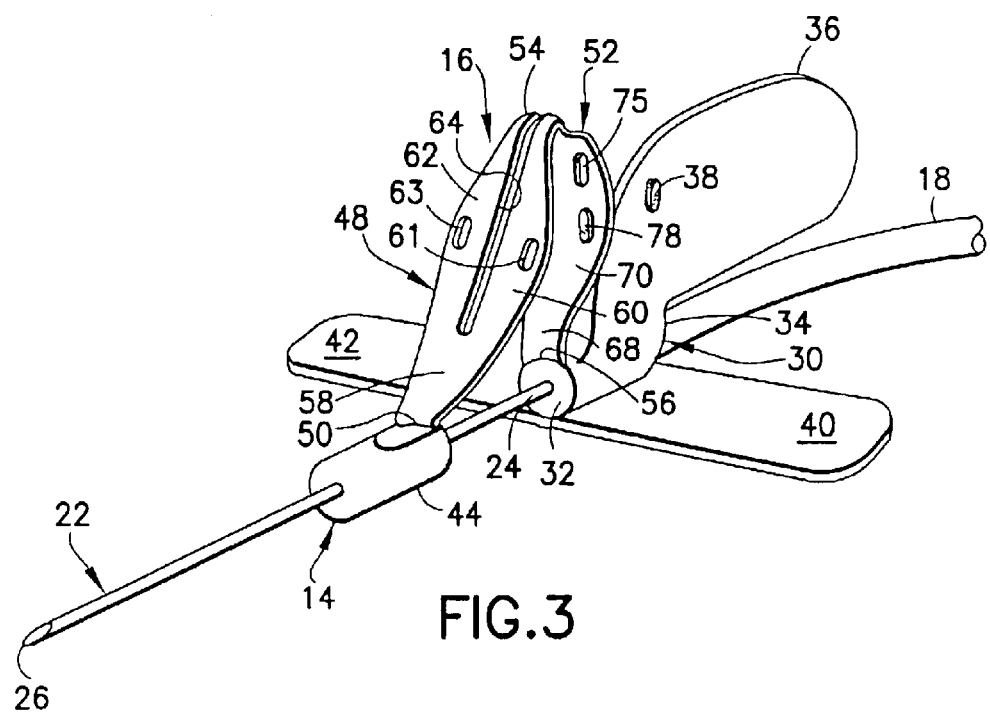
FIG. 3 is a perspective view similar to FIG. 2, but showing the shield in an intermediate position after release of the latch.
Figure 4:
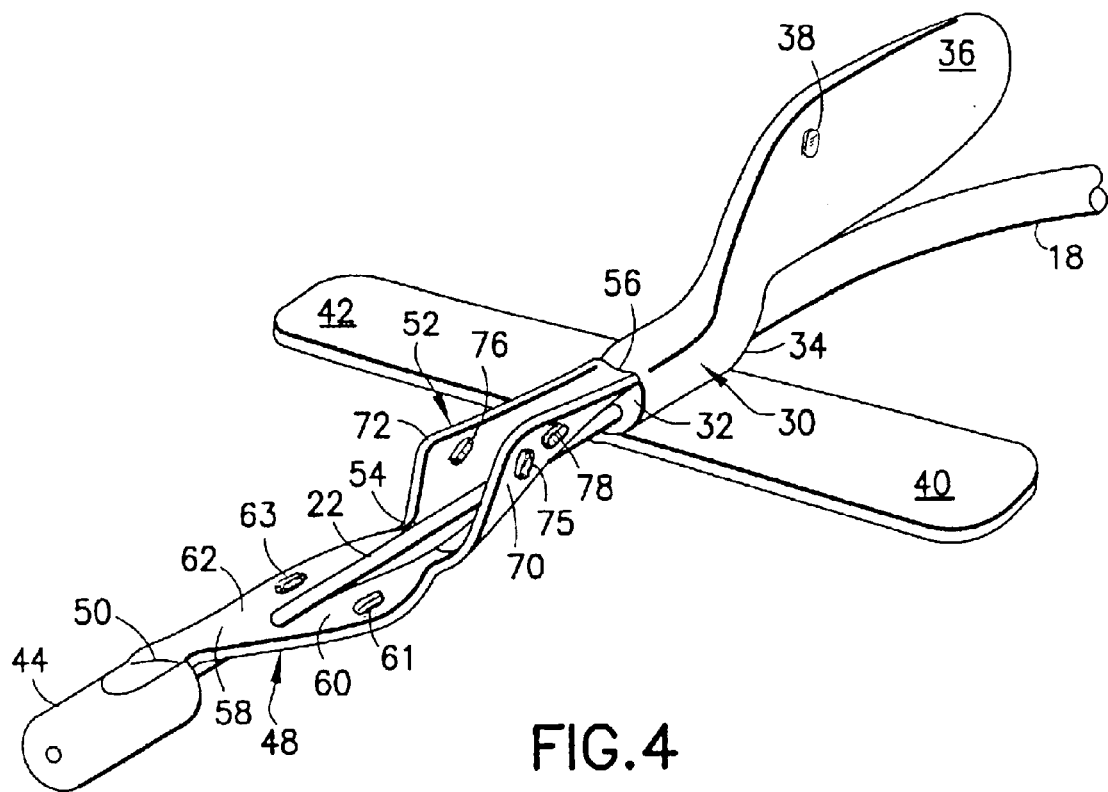
FIG. 4 is a perspective view similar to FIGS. 1 and 3, but showing the wing set in the fully shielded position.

A wing set in accordance with the invention is identified generally by the numeral 10 in FIG. 1. Wing set 10 comprises a needle assembly 12, a shield assembly 14, a tether 16 and a length of flexible plastic tubing 18. Plastic tubing 18 has a distal end 20 connected to needle assembly 12, as explained further below. Plastic tubing 18 further has a proximal end (not shown). The proximal end of plastic tubing 18 may be mounted to a plastic fitting that is used to connect wing set 10 to a container. Thus, wing set 10 can be used to deliver fluid from the container to a patient or to draw fluid from the patient into the container.

Needle assembly 12 includes a needle cannula 22 with a proximal end 24, a distal end 26 that is beveled to a sharp tip and a lumen extending between ends 24 and 26. A safety cap 28 is telescoped over needle cannula 22 and is held in place by other parts of needle assembly 12 or by shield assembly 14 substantially in a known manner. Needle assembly 12 further includes a plastic hub 30. Proximal end 24 of needle cannula 22 is secured in a distal end 32 of hub 30 by adhesive. Hub 30 includes a proximal end 34 with a recess configured for mounting over distal end 20 of plastic tubing 18. Thus, hub 30 permits communication between the lumen of needle cannula 22 and the passage through plastic tubing 18.

Hub 30 further includes a dorsal fin 36 that projects transversely and proximally from proximal end 34 of hub 30. Dorsal fin 36 is substantially planar and is sufficiently sturdy to enable accurate digital manipulation of needle assembly 12. Additionally, dorsal fin 36 is sufficiently large to facilitate convenient gripping of dorsal fin 36 between a thumb and forefinger of a user. Distal portions of dorsal fin 36 are characterized by locking detents 38 that project transversely outwardly from dorsal fin 36.

Hub 30 is further characterized by transverse wings 40 and 42. Wings 40 and 42 are substantially coplanar and are equiangularly spaced from dorsal fin 36. Additionally, wings 40 and 42 preferably are substantially flush with a surface of hub 30 diametrically opposite dorsal fin 36. Thus, wings 40 and 42 and portions of hub 30 diametrically opposite dorsal fin 36 define a smooth continuous surface that can be placed comfortably on the skin of a patient. Dorsal fin 36 and wings 40 and 42 all may be substantially rigid as illustrated in FIGS. 1–5. Thus, all or most digital manipulation of wing set 10 would utilize dorsal fin 36. Wings 40 and 42, on the other hand, would be used primarily for taping wing set 10 adjacent the skin of a patient. Alternatively, wings 40 and 42 may be hingedly rotatable toward one another and into substantially face-to-face engagement with portions of dorsal fin 36. In this latter option, wings 40 and 42 can play a role in the digital manipulation of wing set 10.

Shield assembly 14 comprises a shield housing 44 slidably mounted over needle cannula 22 for movement from a proximal position adjacent hub 30 to a distal position where shield housing 44 surrounds distal end 26 of needle cannula 22. Shield assembly 14 also is provided with a safety latch 46 formed from a metallic material. Latch 46 is secured in shield housing 44 and is biased against a side of needle cannula 22 when shield assembly 14 is in the proximal position shown in FIG. 2. Latch 46 then slides against the side of needle cannula 22 as shield housing 44 is advanced from the proximal position shown in FIG. 2 toward the distal position shown in FIG. 5. When shield assembly 14 reaches the distal position shown in FIG. 5, latch 46 will pass distal tip 26 of needle cannula 22. The inherent biasing forces of latch 46 will urge latch 46 over distal end 26 of needle cannula 22 to prevent re-exposure of needle cannula 22.

Tether 16 includes a distal arm 48 that is connected unitarily to shield housing 44 by a first living hinge 50 that permits hinged movement between distal arm 48 and shield housing 44. A proximal arm 52 is connected unitarily to distal arm 48 by a second living hinge 54. Proximal arm 52 is connected unitarily to hub 30 by a third living hinge 56.

Distal arm 48 includes a base wall 58 that extends from first living hinge 50 to second living hinge 54. Additionally, distal arm 48 includes opposed side walls 60 and 62 that extend from base wall 58 at locations between first and second living hinges 50 and 54. Thus, at least portions of distal arm 48 are generally channel-shaped. Side walls 60 and 62 are formed respectively with locking recesses 61 and 63. Base wall 58 of distal arm 48 is characterized by a central slot 64 that extends from second living hinge 54 toward first living hinge 50. Slot 64 is sufficiently wide to accommodate needle cannula 22.

Proximal arm 52 is similarly channel shaped, and includes a base wall 68 and opposed side walls 70 and 72, and hence also is generally channel shaped. A slot 74 is formed in base wall 68 of proximal arm 52 and extends from second living hinge 54 toward third living hinge 52. Slot 74 is sufficiently wide to accommodate needle cannula 22 therein. Additionally, slots 64 and 74 are continuous with one another across second living hinge 54. Living hinges 50, 54 and 56 are biased toward a substantial linear alignment of shield housing 44, distal arm 48, proximal arm 42 and hub 30. However, living hinges 50, 54 and 56 permit proximal arm 52 to be nested over distal portions of dorsal fin 36 and permit distal arm 48 to be nested over portions of proximal arm 52 as shown in FIGS. 1 and 2. In this orientation, shield 44 is disposed substantially adjacent hub 30. Side walls 70 and 72 of proximal arm 52 are formed respectively with locking recesses 74 and 76. Locking recesses 74 and 76 are disposed to engage locking detents 38 when proximal arm 52 is rotated about the third living hinge 56 and into nested disposition over distal portions of dorsal fin 36. Proximal arm 52 also is formed with an outwardly projecting detent 78 on side wall 70 and an identical detent (not shown) on side wall 72. The detents on side walls 70 and 72 of proximal arm 52 are dimensioned and disposed to engage locking recesses 61 and 63 on side walls 60 and 62 of distal arm 48 when arms 48 and 52 are collapsed onto one another. As shown most clearly in FIG. 2, dorsal fin 36 is shorter than distal and proximal arms 48 and 52. Thus portions of distal and proximal arms 48 and 52 adjacent the second living hinge 54 project above dorsal fin 36 when distal and proximal arms 48 and 52 are collapsed into nested disposition over dorsal fin 36.

Wing set 10 is employed substantially in a conventional manner. More particularly, the dorsal fin 36 of wing set 10 can be gripped between a thumb and forefinger. A health care worker then engages safety cap 28 with the opposed hand and separates safety cap 28 from needle cannula 22. The health care worker then maintains a grip on dorsal fin 36 and guides pointed distal end 26 of needle cannula 22 into a targeted location on a patient. Wings then can be held in the selected location, if necessary, by taping wings 40 and 42 to the skin of the patient.

After use, the health care worker re-grips dorsal fin 36 with a thumb and forefinger and withdraws needle cannula 22 from the patient. The healthcare worker then exerts distally directed forces on portions of proximal arm 52 that project above dorsal fin 36. These distally directed forces overcome the engagement forces between locking detents 38 on dorsal fin 36 and locking recesses 74 and 76 in side walls 70 and 72 of proximal arm 52. Similarly, these distally directed forces overcome the engagement forces between locking detents 78 on side walls 70 and 72 of proximal arm 52 and the locking recesses 61 and 63 on the side walls 60 and 62 of distal arm 48. The release of the locking recesses from locking the detents causes the inherent biasing forces in living hinges 50, 54 and 58 to urge distal and proximal arms 48 and 52 from the collapsed condition shown in FIGS. 1 and 2 into the partly open condition shown in FIG. 3 and eventually into the fully extended linear orientation shown in FIGS. 4 and 5. This movement causes shield assembly 14 to slide distally along needle cannula 22. Additionally, intermediate portions of needle cannula 22 pass into slots 64 and 74. Side walls 60 and 62 of distal arm 48 and side walls 70 and 72 of proximal arm 52 achieve a partial shielding of intermediate portions of needle cannula 22. Shield 44 is positioned over needle cannula 22 when arms 48 and 52 are in the fully extended condition shown in FIGS. 4 and 5. Additionally, latch 46 springs over distal tip 26 of needle cannula 22 to prevent a return proximal movement of shield assembly 14 that would re-expose distal tip 26 of needle cannula 22. Thus, latch 46 prevents proximal movement of shield assembly 14 while arms 48 and 52 prevent distal movement of shield assembly 14. Wing set 10 then can be disposed of safely in a sharps receptacle.

The embodiment described above and illustrated herein depicts distal and proximal arms 48 and 52 being unitary with one another and unitarily joined to shield housing 44 and hub 30 by the living hinges. However, the shield, arms and hub may be formed separately and connected to one another by hinge pins. Additionally, the embodiment described above and illustrated herein discloses the inherent resiliency of living hinges 50, 54 and 56 being sufficient to propel shield 44 distally and into shielding disposition over distal end 26 of needle cannula 22. However, the wing set of the subject invention may rely entirely upon digital forces to move distal and proximal arms 48 and 52 into the extended position. Alternatively separate springs may be provided for urging shield assembly 14 distally relative to hub 30. For example, a coil spring can be mounted around and/or parallel to cannula 22. The coil spring may be in a collapsed stored-energy condition prior to use. However, this engagement of locking recesses 74 and 76 from locking projections 38 will release the energy stored in the coil spring and propel shield 44 distally along needle cannula 22 and into the position shown in FIGS. 4 and 5. As a further alternate, the torsion spring may be incorporated at least into one of the hinged connections of distal and proximal arms 48 and 52 similar to the arrangement shown in U.S. Pat. No. 5,348,544.

What is claimed is:

1. A safety needle assembly comprising:
   a hub having proximal and distal ends and a passage extending between said ends;
   a needle cannula having a proximal end mounted in said hub and a pointed distal end projecting distally from said hub;
   a shield slidably mounted on said needle cannula and movable from a proximal position where said pointed distal end of said needle cannula is exposed to distal position where said shield is in a shielding disposition relative to said distal end of said needle cannula;
   a substantially planar fin projecting from said hub for facilitating digital manipulation of said needle assembly, wherein said fin remains in a fixed position relative to said needle cannula, when said shield moves from said proximal position to said distal position;
   a proximal arm having a proximal end hinged to at least one of said hub and said fin and a distal end, said proximal arm being hingedly rotated from a first position adjacent said fin to a second position substantially adjacent said needle cannula, said proximal arm having locks for releasably engaging said fin; and
   a distal arm having a proximal end hinged to said distal end of said proximal arm and having a distal end hinged to said shield, said distal arm being substantially adjacent said cannula when said proximal arm is rotated into said second position, wherein rotation of said proximal arm into said second position moves said shield into the shielding disposition relative to said distal end of said needle cannula.

2. The safety needle assembly of claim 1, wherein said proximal and distal arms have lengths for preventing movement of said shield distally beyond said needle cannula.

3. The safety needle assembly of claim 2, wherein said shield includes a spring clip biased against said needle cannula when said shield is in said proximal position and when said shield is moving toward said distal position, said spring clip moving over said distal end of said needle cannula when said shield is in said distal position for preventing said shield from moving proximally from said distal position.

4. The safety needle assembly of claim 1, wherein said proximal and distal arms are formed unitarily with one another.

5. The safety needle assembly of claim 4, wherein said proximal arm is formed unitarily with said hub.

6. The safety needle assembly of claim 5, wherein said distal arm is formed unitarily with at least a portion of said shield.

7. The safety needle assembly of claim 1, wherein said proximal and distal arms have lengths selected such that said distal end of said proximal arm projects beyond said fin when said proximal arm is in said first position.

8. The needle assembly of claim 1, further comprising a length of flexible plastic tubing connected to said proximal end of said hub and communicating with said needle cannula.

9. A safety needle assembly comprising:
   a hub having proximal and distal ends and a passage extending between said ends;
   a needle cannula having a proximal end mounted in said hub and a pointed distal end projecting from said hub:
   a shield slidably mounted on said needle cannula and movable from a proximal position where said pointed distal end of said needle cannula is exposed to distal position where said shield is in a shielding disposition relative to said distal end of said needle cannula;
   a fin projecting from said hub for facilitating digital manipulation of said needle assembly;
   a proximal arm having a proximal end hinged to at least one of said hub and said fin and a distal end, said proximal arm being hingedly rotated from a first position adjacent said fin to a second position substantially adjacent said needle cannula, wherein said proximal arm is releasably locked to said fin by at least one detent projecting from at least one of said fin and said proximal arm and at least one locking recess formed in the other of said fin and said proximal arm, said detent and said recess releasably holding the proximal arm in said first position; and
   a distal arm having a proximal end hinged to said distal end of said proximal arm and having a distal end hinged to said shield, said distal arm being substantially adjacent said cannula when said proximal arm is rotated into said second position, wherein rotation of said proximal arm into said second position moves said shield into the shielding disposition relative to said distal end of said needle cannula.

10. The safety needle assembly of claim 9, wherein said distal arm is releasably locked with said proximal arm when said proximal arm is in said first position, the releasable locking including at least a second detent formed on at least said one of said proximal and distal arms and at least a second locking recess formed in the other of said proximal and distal arms, said second locking detent and said second locking recess being releasably engaged with one another when said proximal arm is in said first position.

11. The safety needle assembly of claim 1, further comprising biasing means for biasing said shield from said proximal position to said distal position.

12. The needle assembly of claim 11, wherein the biasing means comprises a resiliently biased living hinge between said proximal arm and said hub.

13. A safety needle assembly comprising:
   a hub having proximal and distal ends and a passage extending between said ends;
   a needle cannula having a proximal end mounted in said hub and a pointed distal end projecting from said hub;
   a shield slidably mounted on said needle cannula and movable from a proximal position where said pointed distal end of said needle cannula is exposed to distal position where said shield is in a shielding disposition relative to said distal end of said needle cannula;
   a fin projecting from said hub for facilitating digital manipulation of said needle assembly;
   a proximal arm having a proximal end hinged to at least one of said hub and said fin and a distal end, said proximal arm being hingedly rotated from a first position adjacent said fin to a second position substantially adjacent said needle cannula, said proximal arm having locks for releasably engaging said fin;

a distal arm having a proximal end hinged to said distal end of said proximal arm and having a distal end hinged to said shield, said distal arm being substantially adjacent said cannula when said proximal arm is rotated into said second position, wherein rotation of said proximal arm into said second position moves said shield into the shielding disposition relative to said distal end of said needle cannula; and a pair of wings projecting transversely from said hub.

14. The needle assembly of claim 13, wherein the wings are rotatable from a first position where said wings are substantially coplanar and substantially orthogonal to said fin and a second position where said wings are engageable with opposite sides of said fin.

15. The A safety needle assembly comprising:

a hub having proximal and distal ends and a passage extending between said ends;

a needle cannula having a proximal end mounted in said hub and a pointed distal end projecting from said hub;

a shield slidably mounted on said needle cannula and movable from a proximal position where said pointed distal end of said needle cannula is exposed to distal position where said shield is in a shielding disposition relative to said distal end of said needle cannula;

a fin projecting from said hub for facilitating digital manipulation of said needle assembly;

a proximal arm having a proximal end hinged to at least one of said hub and said fin and a distal end, said proximal arm being hingedly rotated from a first position adjacent said fin to a second position substantially adjacent said needle cannula, said proximal arm having locks for releasably engaging said fin; and a distal arm having a proximal end hinged to said distal end of said proximal arm and having a distal end hinged to said shield, said distal arm being substantially adjacent said cannula when said proximal arm is rotated into said second position, wherein rotation of said proximal arm into said second position moves said shield into the shielding disposition relative to said distal end of said needle cannula, wherein said proximal and distal arms each include a central slot passing therethrough, said slot being dimensioned to permit passage of said needle cannula as said proximal arm is moved from said first position to said second position.

16. A safety needle assembly comprising:

a hub with a proximal end, a distal end and a passage extending between said ends;

a needle cannula having a proximal end mounted in said passage through said hub, a sharply pointed distal end projecting distally beyond said hub and a lumen extending between said ends and communicating with said passage through said hub;

a dorsal fin projecting from said hub substantially normal to said passage through said hub;

wings projecting transversely from said hub and movable from a first position where said wings are substantially coplanar and substantially orthogonal to said dorsal fin and a second position where said wings engage opposite sides of said dorsal fin;

a proximal arm hinged unitarily to at least one of said hub and fin and rotatable from a first position where said proximal arm is releasably engaged with said dorsal fin and a second position where said proximal arm is substantially adjacent said needle cannula, said proximal arm being biased toward said second position;

a distal arm having a proximal end hinged unitarily to a portion of said proximal arm remote from said hub and an opposed distal end; and a shield housing hinged unitarily to said distal end of said distal arm and slidably moveable along said needle cannula from a proximal position spaced from said pointed distal end of said needle cannula when said proximal arm is in said first position and a distal position for shielding said distal end of said needle cannula when said proximal arm is in said second position.

17. The needle assembly of claim 16, wherein said proximal arm and said dorsal fin are formed with interengaged locking structures for releasably holding said proximal arm in said first position.

18. The needle assembly of claim 17, wherein said proximal arm and said distal arm have interengaged locking structures for holding said distal arm substantially adjacent said proximal arm when said proximal arm is in said first position.

19. The needle assembly of claim 16, wherein said distal arm projects transversely from said hub beyond said dorsal fin for providing an actuation region for receiving digital forces for releasing the locked engagement of said proximal arm to said dorsal fin when said proximal arm is in said first position.

20. The needle assembly of claim 16, wherein said proximal and distal arms include a slot, at least portions of said needle cannula passing through said slot as said shield housing is moved from said proximal position to said distal position.

21. The needle assembly of claim 16, further comprising a spring clip mounted in said shield housing and biased against said needle cannula when said shield clip is in said proximal position and when said shield is moving toward said distal position, spring being deflected over said distal end of said needle cannula when said shield is in said distal position.

* * * * *

UNITED STATES PATENT AND TRADEMARK OFFICE
CERTIFICATE OF CORRECTION

PATENT NO. : 6,918,891 B2
DATED : July 19, 2005
INVENTOR(S) : Peter Bressler et al.

It is certified that error appears in the above-identified patent and that said Letters Patent is hereby corrected as shown below:

<u>Title page,</u>
Insert Item -- [73] Assignee: Becton Dickinson and Company, Franklin Lakes, NJ --.

Signed and Sealed this

Ninth Day of May, 2006

JON W. DUDAS
*Director of the United States Patent and Trademark Office*